United States Patent [19]

Umbach et al.

[11] E Re. 29,243

[45] Reissued May 31, 1977

[54] POLYALKYLENE GLYCOL ETHERS OF HYDROXYALKYLMERCAPTANS AND PROCESS

[75] Inventors: Wilfried Umbach, Langenfeld; Rainer Mehren, Wesel; Werner Stein, Erkrath-Unterbach, all of Germany

[73] Assignee: Henkel & Cie G.m.b.H., Dusseldorf-Holthausen, Germany

[22] Filed: May 19, 1975

[21] Appl. No.: 578,546

Related U.S. Patent Documents

Reissue of:

[64] Patent No.: 3,661,851
Issued: May 9, 1972
Appl. No.: 863,350
Filed: Oct. 2, 1969

[30] Foreign Application Priority Data

Oct. 8, 1968 Germany ..... 1801712

[52] U.S. Cl. ..... 260/609 R; 252/89 R; 252/135; 252/319; 252/352; 260/609 F

[51] Int. Cl.[2] ..... C07C 149/18

[58] Field of Search ..... 260/609 F, 609 R

[56] References Cited

UNITED STATES PATENTS

| | | | |
|---|---|---|---|
| 2,626,924 | 1/1953 | DeGroote | 260/609 F |
| 2,900,368 | 8/1959 | Stilman | 260/609 A |
| 3,335,189 | 8/1967 | Degener et al. | 260/609 R |
| 3,427,248 | 2/1969 | Lamberti et al. | 260/609 F |
| 3,661,851 | 5/1972 | Umbach et al. | 260/609 F |
| 3,662,003 | 5/1972 | Umbach et al. | 260/609 R |
| 3,662,004 | 5/1972 | Umbach et al. | 260/609 R |
| 3,708,543 | 1/1973 | Hickner et al. | 260/609 R |
| 3,758,595 | 9/1973 | Lamberti et al. | 260/609 R |

OTHER PUBLICATIONS

Danehy et al.: "J.A.C.S.," vol. 82 (1960), pp. 2511–2515.

*Primary Examiner*—Delbert R. Phillips
*Attorney, Agent, or Firm*—Hammond & Littell

[57] ABSTRACT

Polyalkylene glycol ethers of β-hydroxymercaptans of the formula

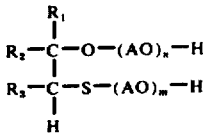

wherein $R_1$ is a member selected from the group consisting of alkyl having from 1 to 22 carbon atoms, alkoxyalkyl having from 2 to 22 carbon atoms, haloalkyl having from 1 to 22 carbon atoms, cycloalkylalkyl having from 6 to 22 carbon atoms and alkenyl having from 3 to 22 carbon atoms, $R_2$ and $R_3$ are members selected from the group consisting of hydrogen, and $R_1$ and when taken together alkylene having from 3 to 4 carbon atoms, with the proviso that the sum of the carbon atoms in $R_1$, $R_2$ and $R_3$ is from 4 to 22; A is a bivalent member having from 2 to 4 carbon atoms selected from the group consisting of alkylene, haloalkylene and hydroxyalkylene; n is an integer from 0 to 50; m is an integer from 1 to 50; and the sum of n and m is an integer from 1 to 50. The compounds have surface-active properties and are useful per se or as intermediates.

3 Claims, No Drawings

POLYALKYLENE GLYCOL ETHERS OF HYDROXYALKYLMERCAPTANS AND PROCESS

Matter enclosed in heavy brackets [ ] appears in the original patent but forms no part of this reissue specification; matter printed in italics indicates the additions made by reissue.

THE PRIOR ART

Mercaptans are known to be able to react with epoxides with formation of thioether alcohols. When the reaction is carried out with use of long-chain mercaptans and lower epoxides, products with surface-active properties are obtained.

OBJECT OF THE INVENTION

An object of the present invention is the obtaining of novel polyalkylene glycol ethers of β-hydroxymercaptans of the formula

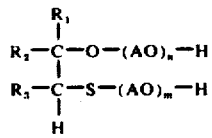

wherein $R_1$ is a member selected from the group consisting of alkyl having from 1 to 22 carbon atoms, alkoxyalkyl having from 2 to 22 carbon atoms, haloalkyl having from 1 to 22 carbon atoms, cycloalkylalkyl having from 6 to 22 carbon atoms and alkenyl having from 3 to 22 carbon atoms, $R_2$ and $R_3$ are members selected from the group consisting of hydrogen and $R_1$, and when taken together alkylene having from 3 to 4 carbon atoms, with the proviso that the sum of the carbon atoms in $R_1$, $R_2$ and $R_3$ is from 4 to 22; A is a bivalent member having from 2 to 4 carbon atoms selected from the group consisting of alkylene, haloalkylene and hydroxyalkylene; n is an integer from 0 to 50; m is an integer from 1 to 50; and the sum of n and m is an integer from 1 to 50.

Another object of the invention is the development of a process for obtaining the above polyalkylene glycol ethers of β-hydroxymercaptans by alkoxylation.

These and other objects of the invention will become more apparent as the description thereof proceeds.

DESCRIPTION OF THE INVENTION

We have now discovered novel polyalkyleneglycol ethers of polyalkylene glycol ethers of β-hydroxymercaptans of the formula

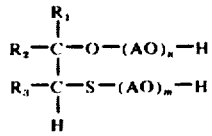

wherein $R_1$ is a member selected from the group consisting of alkyl having from 1 to 22 carbon atoms, alkoxyalkyl having from 2 to 22 carbon atoms, haloalkyl having from 1 to 22 carbon atoms, cycloalkylalkyl having from 6 to 22 carbon atoms and alkenyl having from 3 to 22 carbon atoms, $R_2$ and $R_3$ are members selected from the group consisting of hydrogen and $R_1$, and when taken together alkylene having from 3 to 4 carbon atoms, with the proviso that the sum of the carbon atoms in $R_1$, $R_2$ and $R_3$ is from 4 to 22; A is a bivalent member having from 2 to 4 carbon atoms selected from the group consisting of alkylene, haloalkylene and hydroxyalkylene; n is an integer from 0 to 50; m is an integer from 1 to 50; and the sum of n and m is an integer from 1 to 50. These compounds have not hitherto been known.

These novel polyalkylene glycol ethers of β-hydroxymercaptans are non-ionic surface active compounds which are utilizable as wetting agents, emulsifying agents or detergent substances, depending on the chain length of the alkyl residue present in the initial mercaptan and the number of alkylene oxide groups added on.

A preferred aspect of the present invention is the novel polyalkylene glycol ethers of β-hydroxymercaptans of the formula

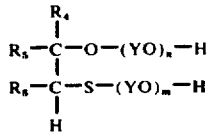

wherein $R_4$ is an alkyl having from 1 to 22 carbon atoms, $R_5$ and $R_6$ are members selected from the group consisting of hydrogen and alkyl having from 1 to 21 carbon atoms, preferably hydrogen, with the proviso that the sum of the carbon atoms in $R_4$, $R_5$ and $R_6$ is from 4 to 22; Y is alkylene having from 2 to 4 carbon atoms; n is an integer from 0 to 50, preferably 1 to 30; m is an integer from 1 to 50, preferably from 2 to 30 and the sum of n and m is an integer from 1 to 50, preferably 4 to 30.

In a further aspect, the present invention therefore provides a process for the production of sulfur-containing alkylene oxide adducts with improved surface-active properties comprising reacting a mercaptan having from 6 to 24 carbon atoms, which carries a hydroxyl group on the carbon atom adjacent to the SH group, with an alkylene oxide having 2 to 4 carbon atoms, in the molar ratio 1:1 to 1:50.

Suitable starting substances are aliphatic and cycloaliphatic β-hydroxymercaptans, especially aliphatic β-hydroxyalkylmercaptans with terminal mercapto groups. The alkyl chains of these aliphatic β-hydroxyalkylmercaptans may contain double bonds, be branched or substituted or interrupted by cycloaliphatic and/or aromatic groups. The alkyl chains may also be substituted and/or interrupted by hetero atoms or hetero atom groups, which do not interfere with the alkoxylation reaction, for example halogen atoms or ether groups.

It is preferred to use terminal β-hydroxyalkylmercaptans with straight-chain, saturated, aliphatic alkyl residues as starting substances, for example, 1-mercapto-2-hydroxyhexane, 1-mercapto-2-hydroxyoctane, 1-mercapto-2-hydroxydodecane, 1-mercapto-2-hydroxydocosane, 1-mercapto-2-hydroxytetracosane.

β-hydroxymercaptans are formed when the epoxide ring is opened by means of hydrogen sulfide or metal hydrogen sulfides, β-hydroxyalkylmercaptans with relatively long chains, such as are used as starting substances in the process according to the invention, may be prepared in good yields, for example, by the process according to the copending U.S. Pat. Applications Ser.

Nos. 818,390, now abandoned, and 818,444, both filed Apr. 22, 1969, by reacting corresponding epoxides with hydrogen sulfide in the presence of catalytic amounts of bases.

The alkylene oxides with 2 to 4 carbon atoms to be added on to the β-hydroxymercaptans are, for example, ethylene oxide, propylene oxide, butylene oxide-1,2. Substituted alkylene oxides such as glycide or epichlorhydrin may also be used.

The alkylene oxides may be added on to the β-hydroxyalkyl mercaptans separately, in admixture with one another or successively in any sequence. Such mixed adducts also display foam-regulating effects in addition to surface-active properties.

The amount of the alkylene oxide to be added on depends partly on the number of carbon atoms in the β-hydroxyalkylmercaptan to be used and partly on the particular purpose for which the surface-active substances prepared are to be used. In general, in order to obtain good surface-active properties, and amount of alkylene oxide to be added should be greater, the larger the number of carbon atoms in the β-hydroxyalkylmercaptan. On the other hand, for the preparation of a substance utilizable as a wetting agent from a particular β-hydroxyalkylmercaptan, a smaller amount of alkylene oxide should be added on than in the case when the product is to be used as a cleaning agent.

If the products are to be used as cleaning agents especially as textile cleaning agents, it is advantageous to choose a molar ratio of β-hydroxyalkylmercaptan to alkylene oxide in the range from 1:4 to 1:30, in which particularly favorable results are then obtained when terminal, purely aliphatic β-hydroxyalkylmercaptans with 8 to 18 carbon atoms are reacted with ethylene oxide in this molar ratio.

It is not necessary to use as starting substances β-hydroxyalkylmercaptans of uniform chain lengths either for the last-named or for other uses of the products. The mercaptans may also be used in the form of mixtures, the components of which have alkyl chains of different length but lying within a specified range.

The reaction of the β-hydroxyalkylmercaptans with the alkylene oxides may be carried out in the usual way, for example by reacting the reactants in the presence of basic or acidic catalysts at temperatures of between 0° and 200° C. and at normal or increased pressure. The working up of the products may also be effected in the usual way.

The products of the process are liquid or solid to wax-like substances, depending on the degree of alkoxylation, and have the dissolving behavior characteristics of alkylene oxide adducts. From the chemical standpoint, the products are mixtures in which, besides such alkylene oxide adducts in which only the mercapto group participated in the reaction, β-hydroxyalkylmercaptans alkoxylated both on the mercapto group and secondary hydroxyl group are present. Separation of the components of the mixture is not generally necessary for the applications described above.

Those products which are sparingly soluble in water, especially lower alkoxylated products, may also serve as starting materials for sulfating reactions. Valuable surface-active compounds are obtained in this way.

The following specific embodiments are illustrative of the practice of the invention without, however, being deemed limitative in any manner.

EXAMPLE 1

54.6 gm (0.25 mol) of 1-mercapto-2-hydroxydodecane, B.P. 114° C./0.03 mm Hg, refractive index $n_D^{25}$=1.4716, OH value (OH- and SH-) 512.1, were mixed with 1.6 gm of sodium methylate in an apparatus comprising a three-necked flask, stirrer, thermometer, gas inlet frit and gas outlet arrangement. After replacing the air by nitrogen, a stock cylinder which contained 82.5 gm (1.0 mols) of ethylene oxide, was connected to the apparatus. After the reaction mixture had been heated to 124° C. the absorption of ethylene oxide began. The final temperature was 154° C. The whole of the ethylene oxide was absorbed in 2 hours and 20 minutes. The residual catalyst was neutralized with dilute acetic acid. The product so obtained contained 7.5 mols of ethylene oxide per mol of 1-mercapto-2-hydroxydodecane.

The product had an OH value of 206.4 (calculated 205) and a turbidity point of 65° C. in 1% aqueous solution. Cotton fabric, which had been artificially soiled with a standard dirt mixture (soot-iron oxide-kaolin-synthetic skin fat) and had a remission value, R=26, was washed with use of this adduct at a bath ratio of 1:12.5 and wash liquors of different concentrations at 90° C., for 15 minutes in each case in a launderometer. Water of 16° German hardness was used for the preparation of the wash liquor. After the washing process, the fabric was rinsed with distilled water three times for 3 minutes in each case, dried and lightly ironed. Then the remission values were measured using a Zeiss-Elrepho instrument (Filter 6) and the percentage brightness was determined therefrom. Analogous washing experiments were carried out with an adduct of 7.4 mols of ethylene oxide to n-dodecylmercaptan (turbidity point of the 1% aqueous solution 67° C.). The results of the washing experiments were as follows:

TABLE I

| | gm of surface-active compound per liter | | | | | |
|---|---|---|---|---|---|---|
| Surface-active compound | 0.5 | 1.0 | 1.5 | 2.0 | 4.0 | |
| 1-mercapto-2-hydroxy-dodecane + 7.5 EO | 45 | 48.5 | 51 | 53 | 53 | Remission value R |
| | 50 | 56.5 | 61 | 64.5 | 64.5 | % brightness |
| 1-mercapto-dodecane + 7.4 EO | 42 | 44 | 44 | 47 | 51 | Remission vaue R |
| | 43.5 | 48 | 48 | 54 | 61 | % brightness |

EO = ethylene oxide

The same washing experiments were carried out with different amounts of surface-active compound in admixture with sodium triphosphate. The washing liquor always contained 1 g. per liter of the combination in question.

TABLE II

| | | | | | | | |
|---|---|---|---|---|---|---|---|
| Surface-active | 100 | 80 | 60 | 40 | 20 | 0 | % surface-active compound |
| compound | 0 | 20 | 40 | 60 | 80 | 100 | % triphosphate |
| 1-mercapto-2-hydroxy-dodecane + 7.5 EO | 48.5 | 51.5 | 59 | 68.5 | 69 | 66 | Remission value R |
| | 56.5 | 62 | 74 | 87.5 | 88 | 84 | % brightness |

TABLE II-continued

| | | | | | | | |
|---|---|---|---|---|---|---|---|
| 1-mercapto-do-decane + 7.4 EO | 44 | 45.5 | 51 | 65.5 | 67.5 | 66 | Remission value R |
| | 48 | 51 | 61 | 83.5 | 86 | 84 | % brightness |

EO = ethylene oxide

These tables demonstrate the improved results in brightness when utilizing the ethoxylated 1-mercapto-2-hydroxy-dodecane as compared with ethoxylated 1-mercapto-dodecane.

EXAMPLE 2

In the procedure according to Example 1, 62.5 gm. (0.25 mol) of a mixture of 1-mercapto-2-hydroxyalkanes, with alkyl radicals of a $C_{11}$ to $C_{18}$ chain-length (OH-number [OH+SH]=450.1), were reacted with 82.5 gm (1.9 mols) of ethylene oxide in the presence of 0.7 gm. of sodium methylate. The amount of ethylene oxide applied was taken up during 2 hours. The product contained on an average 7.7 mols of ethylene oxide per mol of hydroxyalkylmercaptan. The product had a sulfur content of 5.36% and in a 1% aqueous solution a turbidity point of 36° C. The substance has tenside properties and is a very good detergent for wool.

EXAMPLE 3

Example 2 was repeated with the exception that the amount of added ethylene oxide was raised to 10.7 mols of ethylene oxide per mol of hydroxyalkylmercaptan. The amount of ethylene oxide applied was taken up during 5½ hours. The resulting product had a sulfur content of 4.41% and in a 1% solution a turbidity point of 66°–68° C. The product is a tenside which has particularly good detergency for wool and cotton.

EXAMPLE 4

Example 2 was repeated with the exception that the amount of added ethylene oxide was raised to 14 mols of ethylene oxide per mol of hydroxyalkylmercaptan. The amount of ethylene oxide applied was taken up after 4 hours. The addition product had a sulfur content of 3.44% and in a 1% aqueous solution a turbidity point of 94° C. The product has tenside properties and is especially suitable for the washing of cotton and wool.

EXAMPLE 5

In a reaction apparatus equipped with agitator, thermometer, dropping funnel and reflux condenser, 44 gm. (0.2 mol) of 1-mercapto-2-hydroxy-n-dodecane were charged and 0.6 gm. of sodium methylate were added. Through the dropping funnel, 139 gm. (2.4 mols) of propylene oxide were added over 6 hours. The reaction temperature was maintained between 125° C. and 140° C. The resulting product had a sulfur content of 3.3% and a turbidity coefficient of 6.9. The substance is water insoluble and has, in addition to emulsifying properties, a very good foam inhibiting effect in strongly foaming tensile solutions.

EXAMPLE 6

Example 5 was repeated with the exception that the amount of added propylene oxide was raised to 20 mols of propylene oxide per mol of hydroxyalkylmercaptan. The amount of propylene oxide applied was taken up in 8 hours. The resulting product had a sulfur content of 2.1% and a turbidity coefficient of 6.7. The substance is water insoluble and has emulsifying and foam inhibiting properties.

EXAMPLE 7

In the procedure according to Example 5, 44 gm. (0.2 mol) of 1-mercapto-2-hydroxy-n-dodecane were reacted with 144 gm. (2.0 mols) of butylene oxide. The butylene oxide applied was taken up after 7 hours. The reaction temperature was maintained between 120° and 135° C. The resulting product had a sulfur content of 3.2% and a turbidity coefficient of 3.4. The product is water insoluble and a very efficient foam inhibitor in strongly foaming tenside solutions.

EXAMPLE 8

In the procedure according to Example 1, 44 gm. (0.2 mol) of 1-mercapto-2-hydroxy-dodecane were reacted with 282 gm. (6.4 mols) of ethylene oxide in the presence of 1.2 gm. of sodium methylate. The amount of ethylene oxide applied was taken up after 6 hours. The resulting product was subsequently, according to the procedure of Example 5, reacted with 116 gm. (2.0 mols) of propylene oxide. The propylene oxide applied was taken up after 5 hours. The final product contained an average of 32 mols of ethylene oxide and 10 mols of propylene oxide per mol of hydroxyalkylmercaptan and had a sulfur content of 1.2%. The turbidity point of a 1% aqueous solution was 64° to 66° C. The substance has detergent properties and is especially suited for the washing of cotton and polyester fibers.

The preceding specific embodiments are illustrative of the practice of the invention. It is to be understood, however, that other procedures known to those skilled in the art may be employed without departing from the spirit of the invention.

We claim:

1. Polyalkylene glycol ethers of β-hydroxymercaptans of the formula

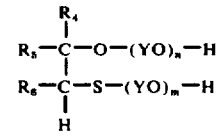

wherein $R_4$ is an alkyl having from 1 to 22 carbon atoms, $R_5$ and $R_6$ are members selected from the group consisting of hydrogen and alkyl having from 1 to 21 carbon atoms, with the proviso that the sum of the carbon atoms in $R_4$, $R_5$ and $R_6$ is from 4 to 22; Y is alkylene having from 2 to 4 carbon atoms; n is an integer from [ 0 to 50 ] *1 to 30*; m is an integer from [ 1 to 50 ] *2 to 30*; and the sum of n and m is an integer from [ 1 to 50 ] *4 to 30*.

2. The polyalkylene glycol ethers of claim 1 wherein $R_5$ and $R_6$ are hydrogen.

[ 3. The polyalkylene glycol ethers of claim 1 wherein the sum of n and m is an integer from 4 to 30 and n is an integer from 1 to 30 and m is an integer from 2 to 30. ]

*4. The polyalkylene glycol ethers of claim 1 wherein Y is ethylene.*

* * * * *